United States Patent [19]

Kreamer

[11] Patent Number: 4,577,631

[45] Date of Patent: Mar. 25, 1986

[54] ANEURYSM REPAIR APPARATUS AND METHOD

[76] Inventor: Jeffry W. Kreamer, 5615 Forest Ave., Des Moines, Iowa 50311

[21] Appl. No.: 671,994

[22] Filed: Nov. 16, 1984

[51] Int. Cl.$^4$ ............................................. A61B 17/12
[52] U.S. Cl. ........................... 128/334 R; 128/303 R; 128/325; 623/1
[58] Field of Search .......... 128/334 R, 334 C, 303 R, 128/325; 3/1.4

[56] References Cited

U.S. PATENT DOCUMENTS

| 3,334,629 | 8/1967 | Cohn | 128/325 |
| 3,540,431 | 11/1970 | Mobin-Uddin | 128/325 X |
| 4,140,126 | 2/1979 | Choudhury | 128/325 |
| 4,456,011 | 6/1984 | Warnecke | 128/325 |
| 4,503,569 | 3/1985 | Dotter | 128/325 X |

Primary Examiner—William H. Grieb

Attorney, Agent, or Firm—Kent A. Herink; G. Brian Pingel

[57] ABSTRACT

A method and apparatus for repairing inside the body a damaged section of a blood vessel, including an occlusion catheter which is inserted into the vessel at an incision site remote from the damaged section. An umbrella-like stopper at the proximal end of the occlusion catheter is positioned upstream of the damaged section whereupon it is opened to block the flow of blood through the damaged section. A prosthetic graft is inserted into the vessel around a balloon catheter. The outer periphery of the graft is coated with a contact adhesive which is brought into contact with the healthy walls of the vessel on either side of the damaged section by inflation of the balloon catheter. The graft adheres permanently to the walls of the vessel thereby replacing the damaged section while leaving the normal circulatory pathways intact.

11 Claims, 10 Drawing Figures

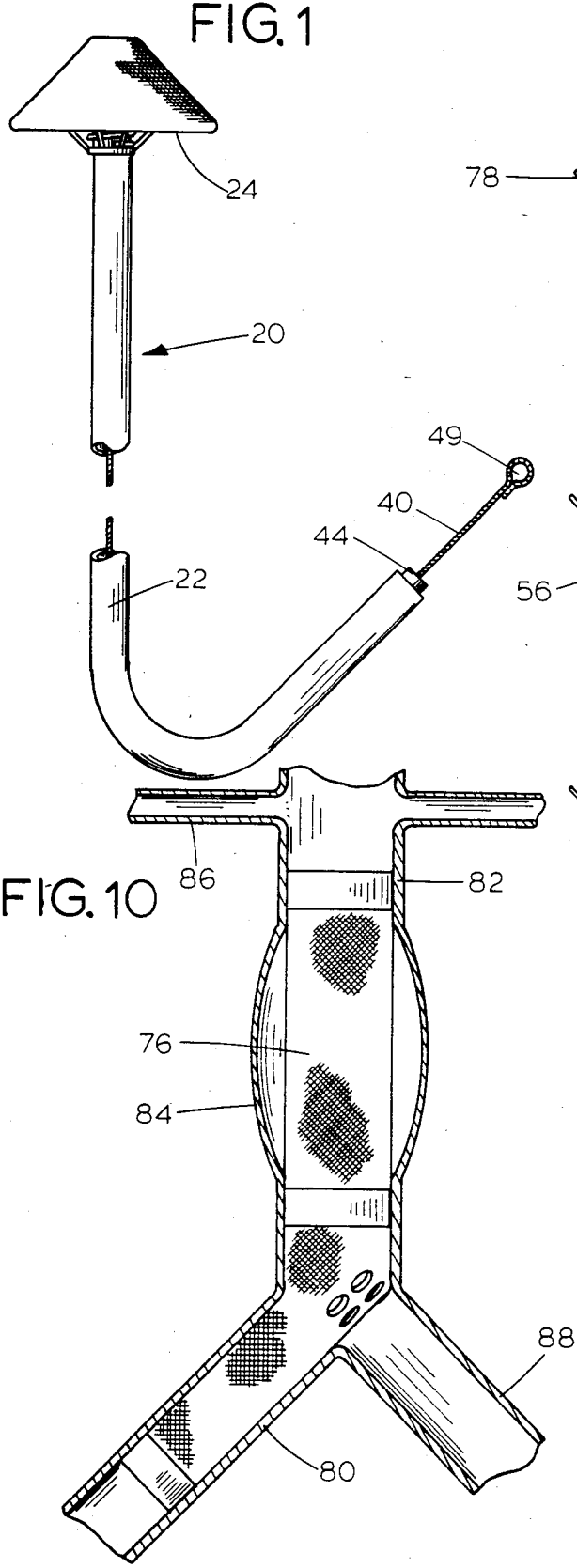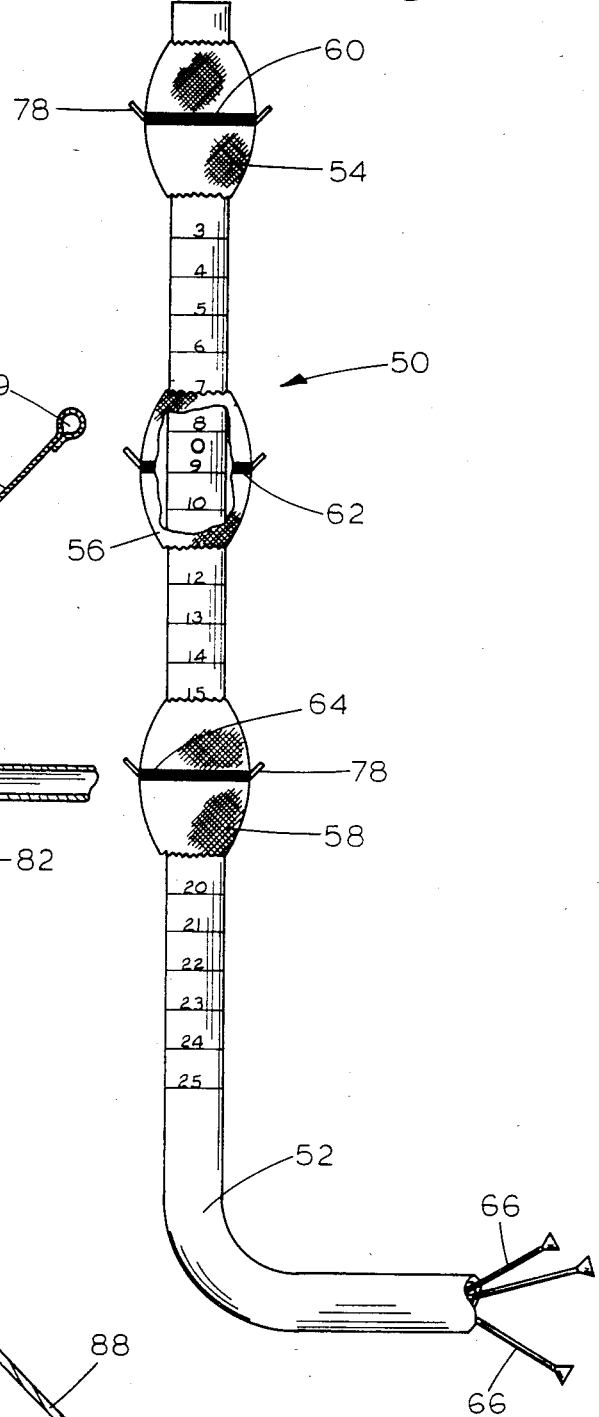

ANEURYSM REPAIR APPARATUS AND METHOD

BACKGROUND OF THE INVENTION

The invention relates generally to an apparatus and method for performing a cardiovascular surgical technique and, more specifically, to an apparatus and method for the significantly less invasive repair of an infra-renal abdominal aortic aneurysm.

Recent statistics state that some 20,000 patients per year are admitted to a hospital only for the treatment of an aortic aneurysm. Another 76,000 patients per year have the treatment of an aortic aneurysm listed as one of the reasons for admission. The pain and danger to life usually associated with aortic aneurysms require some form of surgical treatment in a majority of cases. Generally accepted forms of treatment cause significant trauma to the patient. The two most widely used treatments are resection of the aneurysm or the implementation of an axillobifemoral bypass accompanied by a clotting of the aneurysm. The resection method requires a large incision into the abdominal cavity with surgical insertion of a prosthetic graft inside the damaged section. The surgical invasion of the abdominal cavity greatly increases the complications and mortality which result from the procedure, especially with respect to the majority of those patients with such aneurysms that also exhibit other reasons for hospitalization.

The axillobifemoral bypass method leaves the aneurysm open at the proximal end. The clot of an infra-renal aneurysm may propagate over the renal arteries causing loss of blood flow to the kidneys and possibly resulting in renal failure. Additionally, the grafted artery positioned during the method is very near the surface of the skin where it is susceptible to damage. The substantial rerouting effected by the bypass may also cause complications yet to be identified. Both current treatments are significantly invasive; not infrequently a patient dies during or as a result of the repair surgery.

A less invasive surgical method was recently proposed in U.S. Pat. No. 4,140,126 to Choudhury. The patent teaches a method for repairing an aortic aneurysm using a catheter inserted into the femoral artery and fed up to the site of the aneurysm. The only incision required is relatively small and is made in the leg of the patient. Fluoroscopic or X-ray techniques are used to position the catheter during the surgery. The catheter carries a pair of expanding rings spaced slightly more than the length of the aneurysm. A plurality of anchoring pins, which extend radially of the catheter, are attached to the rings. The prosthetic graft is held by the anchoring pins in a collapsed position smaller than the inside diameter of the artery. Once inserted, the rings are expanded and the anchoring pins penetrate the aortic walls, holding the graft in place with the help of the hemodynamic pressure of blood in the aorta.

The Choudhury method, while much less invasive than the generally accepted surgical techniques, has several distinct disadvantages. The anchoring pins used to hold the graft in place, first on the catheter and then in the aorta, pierce the aortic wall and may cause significant injury to the aorta, especially near the region of the aneurysm that has already severely weakened the aorta. The pins do not reliably hold the graft in position in contact with the walls of the aorta. The method also is carried out while blood continues to flow through the aorta, the aneurysm site, and the femoral artery. Additionally, the graft of Choudhury extends only a very small distance below the site of the aneurysm; the area of healthy vessel to which it must become attached is very small, with the consequence that leakage around the graft may occur or that the graft may not adhere to the vessel.

SUMMARY OF THE INVENTION

The present invention is a method and apparatus for repairing inside the body a damaged section of a blood vessel. An incision is made into the blood vessel at a site remote from and downstream of the damaged section. An occlusion catheter is introduced into the vessel through the incision and is fed up to the area of the damaged section. The occlusion catheter includes at its proximal end a stopper which can be expanded and collapsed with a control system that is external to the patient at the distal end of the catheter. The stopper is accurately positioned by known fluoroscopic or X-ray techniques and is opened above the damaged section to block the flow of blood through the vessel. Gross blood is suctioned from the vessel.

A generally tubular prosthetic graft, having a diameter approximately that of the inside diameter of the healthy section of the vessel, is coated with a contact adhesive that will bond the graft to the vessel walls. The graft is received about a collapsed balloon catheter which is used to insert the graft into position within the vessel. The balloon catheter is then expanded to bring the graft into contact with healthy walls of the vessel on either side of the damaged section. Once the graft is permanently adhered to the vessel walls, the two catheters are withdrawn and the graft permits normal circulation to be returned to the vessel.

The present invention solves many of the problems inherent in known techniques. It provides a method, and the associated apparatus, for repairing an aortic aneurysm without the high risk of major and significantly invasive surgery, with the results that patients can be treated at a lower cost, by less skilled surgeons, in a wider number of facilities, in less time, and with a greater survival rate. Many of the patients who require treatment of an aortic aneurysm have other medical problems which are much less likely to be exacerbated by a procedure which takes a short amount of time and which does not surgically invade the abdominal cavity.

The aneurysm is sealed at both ends before it is clotted so that the clot will not migrate and possibly block the renal arteries, and the natural flow of blood through the aorta is preserved.

Another object of the invention is to provide a method and the necessary apparatus for an improved, less-invasive repair of aortic aneurysms that securely attaches a prosthetic graft to the walls of the aorta without using pins, that blocks the flow of blood through the surgical site during the procedure, and that employs a graft which more securely adheres to the aorta over a larger surface area of healthy portions.

DESCRIPTION OF THE DRAWINGS

FIG. 1 is an elevational view of an aortic occlusion catheter used in performing the method of the invention;

FIG. 8 is an elevational view of a triple balloon catheter used in practicing the method of the invention;

FIG. 10 is a partial, cross-sectional view of the human vascular system near an infra-renal abdominal aortic aneurysm which has been repaired by a prosthetic graft inserted by the method and with the apparatus of the present invention.

DETAILED DESCRIPTION OF A PREFERRED EMBODIMENT

Figure 2:
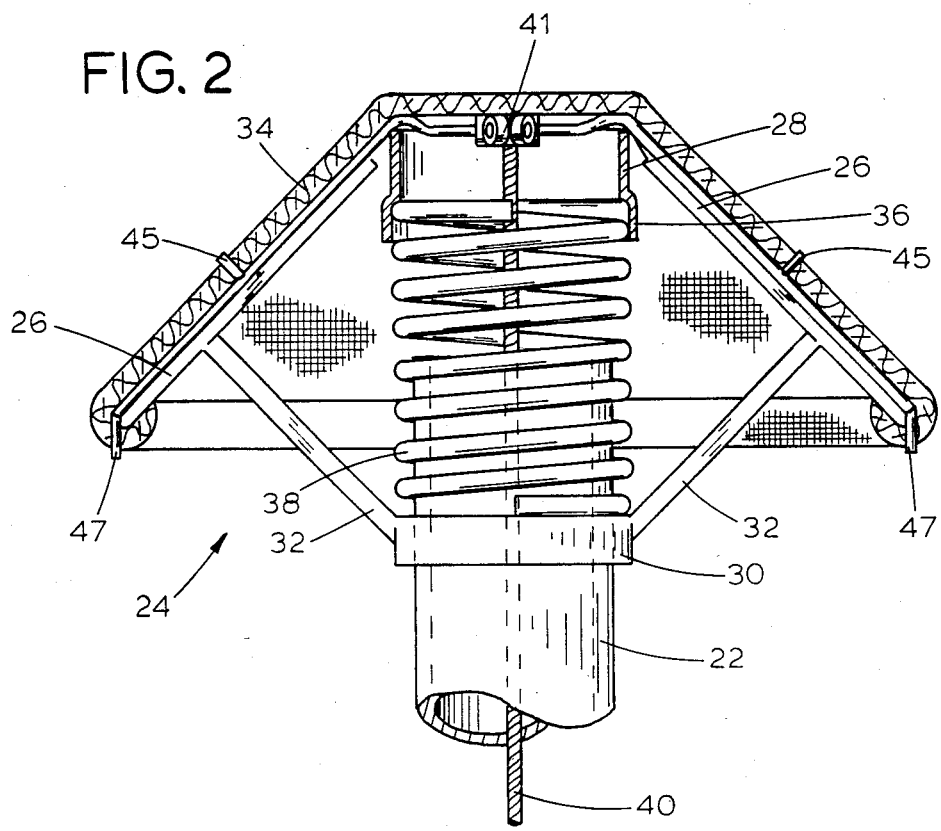
FIG. 2 is an enlarged cross sectional view of the proximal end of the aortic occlusion catheter showing the umbrella structure in a fully opened position.

Illustrated in FIG. 1, generally at 20, is an occlusion catheter comprised of a hollow, flexible tube 22 which terminates with an expandible and collapsible stopper 24. The stopper 24, shown enlarged in FIG. 2, includes a plurality of rib members 26 which are hingedly attached at their inner ends to a forward annular ring 28. A second annular ring 30 is securely mounted about the flexible tube 22 rearwardly of its proximal end. Hingedly attached to the second ring 30 is a plurality of support members 32 equal in number to the plurality of rib members 26. Each of the plurality of support members 32 is hingedly attached to a corresponding one of the rib members 26 at a point approximately one-half to three-fourths of the length of the rib member toward its free end. The entire structure of the two annular rings 28 and 30 and the rib and support members 26 and 32 is comprised of a material, such as high-density polyethylene, which permits the structure to be molded in one piece.

The forward end of the stopper 24 is covered with a nonpourous, flexible cover 34 which is secured to the underside of the free end of each of the rib members 26 and extends over the plurality of rib members 26 and the forward annular ring 28. A retaining ring 36, having an outer periphery which extends outwardly of the periphery of the flexible tube 22, is formed on the forward annular ring 28 and projects rearwardly or distal of the forward ring 28. A helical spring 38 is compressed between the retaining ring 36 of the forward ring 28 and the second ring 30. A hollow control cord 40 is received inside the tube 22 and is securely attached to the cover 34 by a divider 41. The control cord 40 is hollow to permit the introduction at the stopper 24 of radio-opaque dye injected through a saccule or bouton 49 at the distal end of the cord 40. The dye supplied by the cord 40 to the divider 41 is sent thereby to a pair of dye ports 45 and 47 associated with each rib member 26.

Dye ports 45 communicate to the upstream surface of the cover 34, and dye ports 47 direct dye to the periphery of the stopper 24 on the downstream side of the cover 34. The distal end of the control cord 40 extends out of the distal end of the flexible tube 22 (FIG. 1).

Figure 3:
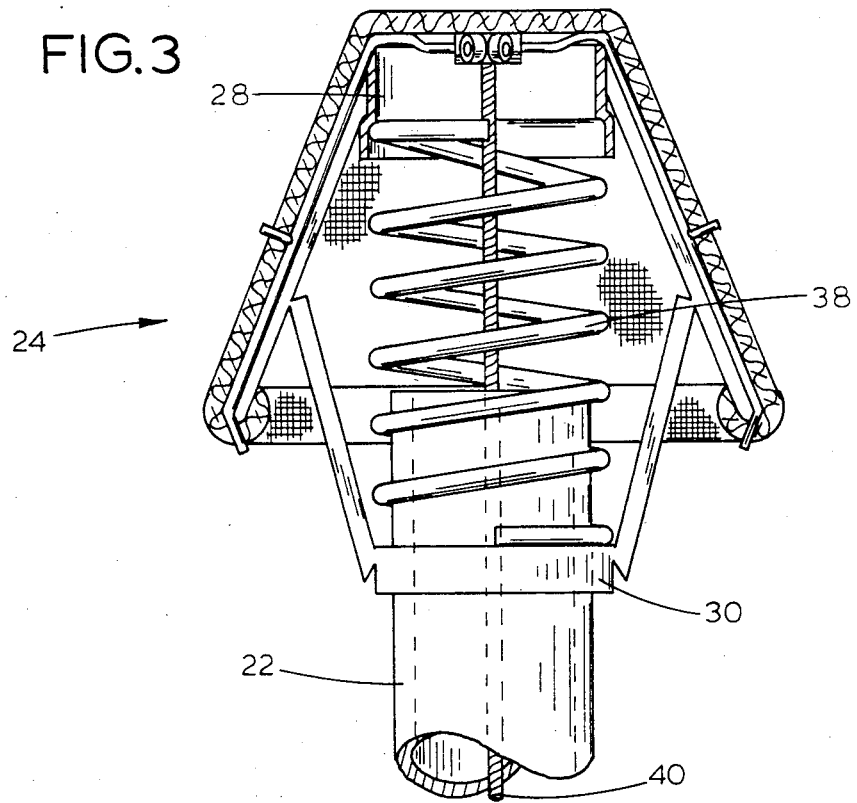
FIG. 3 is an enlarged cross sectional view of the proximal end of the aortic occlusion catheter showing the umbrella structure in a partially opened position.
Figure 4:
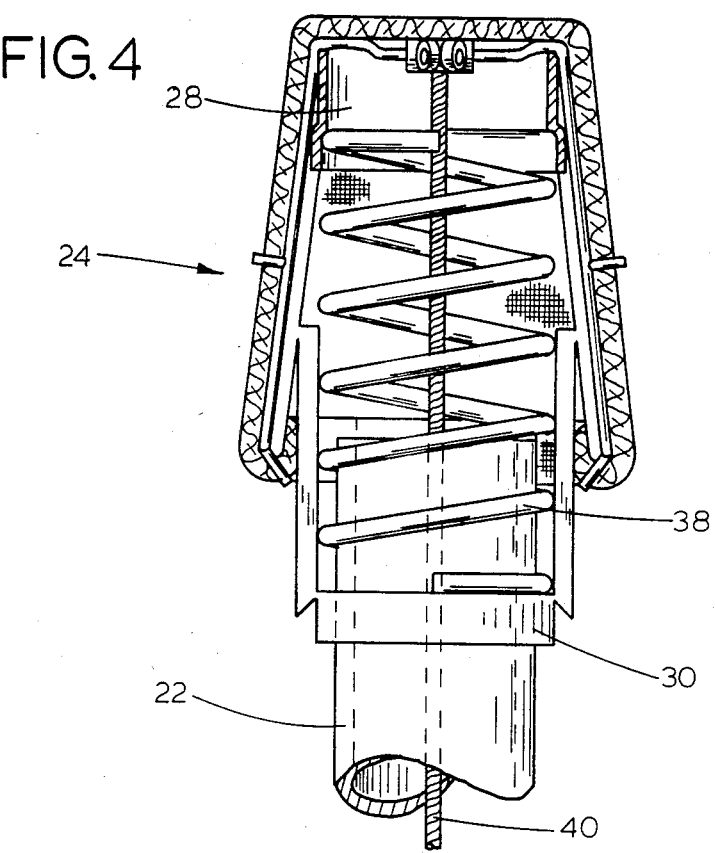
FIG. 4 is an enlarged cross sectional view of the proximal end of the aortic occlusion catheter showing the umbrella structure in a fully closed position.
Figure 5:
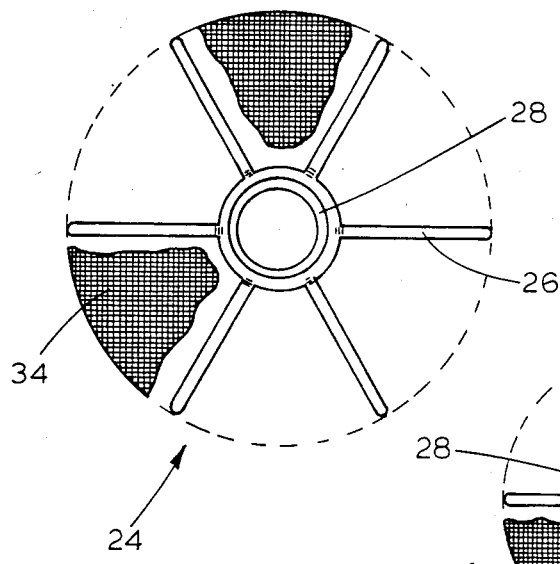
FIG. 5 is an enlarged end view of the umbrella structure of the aortic occlusion catheter in its fully opened position corresponding to that illustrated in FIG. 2.
Figure 6:
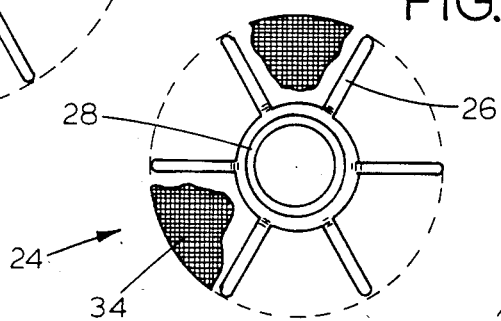
FIG. 6 is an enlarged end view of the umbrella structure of the aortic occlusion catheter in its partially opened position corresponding to that illustrated in FIG. 3.
Figure 7:
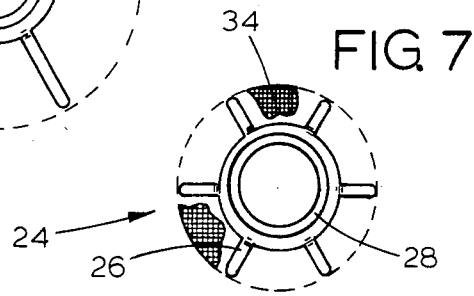
FIG. 7 is an enlarged end view of the umbrella structure of the aortic occlusion catheter in its fully closed position corresponding to that illustrated in FIG. 4.

As illustrated in the sequence of FIGS. 2, 3, and 4, the control cord 40 is used to expand the stopper 24. When there is no tension in the control cord 40, the spring 38 pushes against the forward ring 28 moving it away from the proximal end of the flexible tube 22. The movement of the forward ring 28 collapses the stopper 24, much like an umbrella is collapsed. In reverse manner, when the control cord 40 is pulled to compress the spring 38, the forward ring 28 moves toward the second ring 30 expanding the stopper 24. A chock or clamp 44 (FIG. 1) is used to retain the control cord 40 in a fixed position wherein the stopper 24 is held open to a chosen diameter. The increasing diameter of the stopper 24 with expansion of the stopper 24 by the control cord 40 is best illustrated in the sequence of FIGS. 5, 6 and 7. The transverse diameter of the stopper 24 can be adjusted from less than one centimeter when fully collapsed (FIGS. 4 & 7) to at least four centimeters when fully expanded (FIGS. 2 & 5).

A conventional suction sleeve (not shown) is employed to clean gross blood from the aorta of the patient. In a non-conventional manner, however, during the practice of the method as described later, the sleeve is inserted into the aorta over the occlusion catheter flexible tube 22 after the flow of blood has been blocked by the occlusion catheter 20.

Another part of the apparatus used in performing the method of the invention is a triple balloon catheter, illustrated in FIG. 8, generally at 50. The balloon catheter 50 includes a flexible tube 52 of an inside diameter larger than the outside diameter of the flexible tube 22 of the occlusion catheter 20 (FIG. 1). The tube 52 has graduated markings to facilitate the location of each of three balloons 54, 56, and 58, as will be explained more fully below. Each balloon 54, 56, and 58 is substantially cylindrical with constricted end portions. The opening in the end portions, in their relaxed state, are smaller in diameter than the outer diameter of the flexible tube 52. By stretching each of the balloons, it can be slidably received about the flexible tube 52, as illustrated in FIG. 8. The position of each balloon on the tube 52 is adjusted by sliding the end portions of each balloon to the desired position. The longitudinal midline of each balloon 54, 56, and 58 is marked with a radio-opaque equator at 60, 62, and 64, respectively. The walls of the balloons preferably are thinner toward the equator and thicker at either end so that as the balloons are inflated they expand preferentially at and near the equator rather than near either end.

The balloon catheter tube 52 is divided into three air-tight sections. A color-coded inflation tube 66 extends from each of the sections out the distal end of the catheter 52. The sections may thereby be selectively supplied with compressed air through the appropriate inflation tube. In practicing the method of the invention as described below, the individual balloons 54, 56, and 58 are selectively positioned by the surgeon, one in each section of the catheter 50. Once the positions of the balloons are determined, an air-tight adhesive is applied at the juncture of the balloon and the tube 52 of the catheter 50. When compressed air is introduced into a section through the appropriate inflation tube 66, the corresponding balloon inflates; when the pressure is released, the balloon deflates.

The method of the invention begins with an incision into a blood vessel of the patient that both communicates with the aneurysm to be treated and is downstream from the aneurysm. In the case of an aneurysm of the abdominal aorta, the incision can be made in the femoral artery and no surgical entry need be made into the abdominal cavity. Because the techniques to be described in this specification are of general application and can be adapted by one skilled in the art to treat almost any aneurysm of a major vessel, the detailed description will be limited to the method for treating an infra-renal abdominal aortic aneurysm.

The patient is preferably placed in a reverse Trendelenburg position. The occlusion catheter 20 (FIG. 1) is introduced into a femoral artery, illustrated in FIG. 9 at 78, and is fed up through the iliac artery 80 and into the aorta 82. Known X-ray or flouroscopic techniques are used to determine the exact location of the stopper 24 of the catheter 20 within the aorta. The stopper 24 is positioned upstream of the aneurysm 84 but downstream of the renal arteries 86. It is then opened by pulling the control cord 40. The opened stopper will occlude the vessel, blocking the flow of blood through the aneurysm. Proper placement of the stopper 24 downstream of the renal arteries 86 permits blood to flow uninterrupted to the kidneys. Only the flow of blood to the iliac and femoral arteries is blocked for the duration of the repair surgery. No injury results to the patient from this relatively short impairment of circulation to the legs.

To ensure that the aorta has been occluded and that the renal arteries are open, the occlusion catheter 20 is provided with a plurality of dye ports 45 and 47, each pair of which is associated with each of the rib members 26, in the outer surface of the stopper cover 34 (FIG. 2), as described above. The hollow control cord 40, leading from the distal end of the catheter 20 to the dye ports 45 and 47, is adapted for the injection of a radio-opaque dye into the aorta above and below the stopper 24. On fluoroscope or X-ray examination, the movement of the dye will disclose any seepage around the stopper 24, will show whether the aorta has been completely occluded, and if the renal arteries are being supplied with blood. Readjustment of the stopper 24 should be made if the test determines it was not properly positioned.

Once the aorta is occluded, the suction sleeve (not shown) previously described is inserted into the femoral artery and up into the aorta by riding on the occlusion catheter 20, the tube of the occlusion catheter being slidably received inside the sleeve. Suction is applied to the sleeve and gross blood remaining in the arteries is removed.

Figure 9:
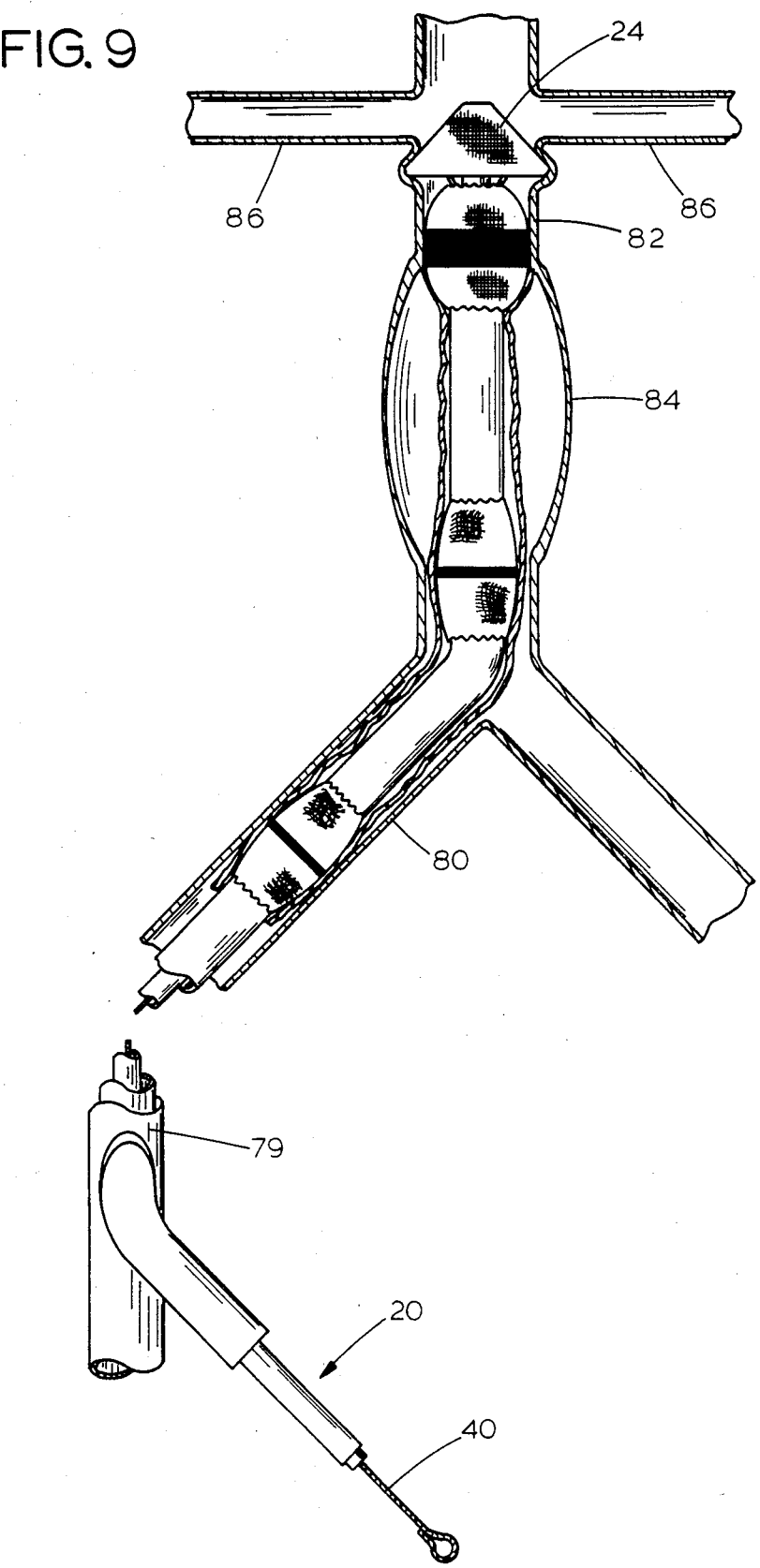
FIG. 9 is a partial, cross-sectional view of the human vascular system near an infra-renal aortic aneurysm and of the occlusion and triple balloon catheters inside the aorta during the practice of the method of the invention.

It is a purpose of the present invention to repair the diseased aorta with a prosthetic graft made of a material, such as Dacron, which is compatible for remaining inside the body of the patient as a prosthetic vessel wall. A prosthetic graft for use in repairing an infra-renal abdominal aortic aneurysm is illustrated in position inside the arteries in FIG. 10 at 76. The graft 76 is generally tubular and of a diameter to match that of the inside diameter of the healthy sections of the patient's arteries, and is preferrably made of double woven Dacron. As illustrated in FIGS. 9 and 10, the diseased section 84 of the aorta 82 may extend very near the bifurcation of the aorta 82 into the two iliac arteries 80 and 88. To ensure that the graft 76 is held securely in place to healthy sections of the arteries, it may be necessary to have the graft 76 extend down the iliac artery 80 towards the femoral artery 79 in which the incision was made. In this case, the graft 76 is fenestrated in the region that would otherwise cover the other iliac artery 88 to permit the normal flow of blood to that limb.

In a preferred embodiment of the invention, the triple balloon catheter 50 (FIG. 8) is employed to insert the prosthetic graft 76 into the aorta 82 (FIGS. 9 and 10). The catheter 50 is inserted into the femoral artery around the tube 22 of the occlusion catheter 20, and is fed up into the aorta until adjacent the stopper 24. Conventional ultrasound or aortographic techniques are used to determine the location of the renal, illiac, and femoral arteries, the size and location of the aneurysm, and the size and extent of the healthy sections of the vessels. The equator 60 of balloon 54 is positioned to be 1 to 3 centimeters above the proximal edge of the aneurysm. The equator 62 of balloon 56 is positioned to be 1 to 3 centimeters below the distal edge of the aneurysm. If it is necessary to have the graft extend below the iliac artery, the balloon 58 is positioned several centimeters below the bifurcation of the iliac arteries. If the healthy section of the aorta below the distal edge of the aneurysm and before the iliac arteries is sufficiently long to ensure adequate contact of the graft, the third balloon 58 is not used. The three balloons 54, 56, and 58 are attached to the balloon catheter 50 at the sites determined by the fluoroscopic examination for proper positioning of the balloons 54, 56, and 58.

The graft 76 is cut to the appropriate length and, if required, fenestrated in the section that would cover the second iliac artery 88 (FIG. 10). A contact adhesive is spread over the entire outer periphery of the graft 76 and the graft is slid over the triple balloon catheter 50. Cyanoacrylate has been found to be a contact adhesive with particularly attractive properties. Cyanoacrylate has little affinity over short contact times for a Dacron-to-Dacron bond. Accordingly, the cyanoacrylate-coated Dacron graft is slidably received over the triple balloon catheter and the proximal end of the graft is removably secured during insertion by a short spikes 78 which project from diametrically opposed points of the equators 62, 64 and 66 of the balloons 54, 56 and 58 of the catheter 50 as shown in FIG. 8. The graft 76 is twisted over on itself to reduce its diameter. A second sleeve, preferably of Dacron or another material with little or no affinity for the cyanoacrylate-coated graft, is then placed over the graft to protect it from contact with the vessel wall during insertion.

The balloon catheter 50 is inserted into the vessel around the tube 22 of the occlusion catheter 20. It is fed up into the aorta to the position previously determined, and illustrated in FIG. 9. The protective sleeve is then gradually removed and the balloons 54, 56, and 58 are sequentially inflated, by the introduction of compressed air into the sections of the catheter tube 52 as described above, as the protective sleeve is withdrawn to expose the adhesive in the area of each balloon. As the balloons 54, 56, and 58 sequentially inflate, the outer periphery of the graft 76 is brought into contact with the walls of the arteries at the positions determined in the prior steps. The cyanoacrylate-covered Dacron graft securely adheres to the walls of the arteries at the contact surfaces. The balloons 54, 56, 58 are now deflated and the balloon catheter 50 is withdrawn.

Once the graft has adhered to the vessel walls, the stopper is collapsed and the occlusion catheter is withdrawn. The incisions in the femoral artery and thigh of the patient are closed.

Modification of the embodiment shown and described will occur to those skilled in the art. For example, while it is preferable to have dye ports in the cover of the stopper of the occlusion catheter, diagnostic techniques may improve to permit the locations within the body to be determined without the use of radioopaque dyes. Accordingly, the occlusion catheter may be replaced by an occlusion device having a solid flexible stem not intended for the transport of fluids. Further, other methods of activating the adhesive only after the graft has been positioned inside the aorta, such as ultraviolet activation or using ultrasound to activate encapsulated adhesives, may be used without departing from the present invention. The scope of the invention presented herein is limited only as defined in the following claims.

I claim:

1. A method for repairing inside the body a damaged section of a blood vessel, comprising the steps of:
   a. making an incision into a vessel distal of and communicating with the damaged section of the blood vessel;
   b. blocking the flow of blood through the vessel and the damaged section by inserting an occlusion catheter into the vessel through the incision and opening the catheter upstream of the damaged section of the vessel;
   c. feeding into the vessel a prosthetic graft affixed temporarily to a second catheter, which graft extends longitudinally beyond the damaged section to healthy portions of the vessel; and
   d. adhering the graft to healthy sections of the vessel on either side of the damaged section by an adhesive on the outer periphery of the graft which is contacted to the vessel by the second catheter.

2. A method for repairing within the body a damaged portion of a blood vessel, comprising the steps of:
   a. inserting an occlusion catheter into an incision in a vessel downstream from and communicating with the damaged portion of the blood vessel;
   b. blocking the flow of blood through the vessel by expanding the occlusion catheter upstream from the damaged portion;
   c. inserting a generally tubular prosthetic graft into the vessel, which graft extends longitudinally beyond the damaged portion to healthy portions of the vessel; and
   d. adhering the prosthetic graft to healthy walls of the vessel by a adhesive applied to the outer periphery of the graft and contacted to the vessel by an expandable catheter.

3. The method for repairing inside the body a damaged section of a blood vessel as defined in claim 1, wherein:
   a. the damaged section is an infra-renal abdominal aortic aneurysm;
   b. the incision is made in one of the femoral arteries; and
   c. the occlusion catheter is opened upstream of the aneurysm but downstream of the renal arteries.

4. The method for repairing inside the body a damaged section of a blood vessel as defined in claim 3, wherein:
   a. the graft is adhered to the aorta downstream of the renal arteries but upstream of the aneurysm, and downstream of the aneurysm, but upstream of the iliac arteries.

5. The method for repairing inside the body a damaged section of a blood vessel as defined in claim 3, wherein:
   a. the graft extends into the iliac arteries and is fenestrated to permit flow of blood to both iliac arteries; and
   b. the graft is adhered to the aorta downstream of the renal arteries but upstream of the aneurysm, to the aorta downstream of the aneurysm, but upstream of the iliac arteries, and to one of the iliac arteries downstream of the bifurcation of the aorta into the iliac arteries.

6. The method for repairing inside the body a damaged section of a blood vessel as defined in claim 3, wherein:
   a. the graft extends into the iliac arteries and is fenestrated to permit flow of blood to both iliac arteries; and
   b. the graft is adhered to the aorta downstream of the renal arteries but upstream of the aneurysm, and to one of the iliac arteries downstream of the bifurcation of the aorta into the iliac arteries.

7. The method for repairing inside the body a damaged section of a blood vessel as defined in claim 1, further comprising:
   a. covering temporarily the outer periphery of the graft with a protective sleeve which is withdrawn after feeding of the graft in the vessel to expose the outer periphery of the graft for contact to the vessel by the second catheter.

8. Apparatus for repairing within the body a damaged section of a blood vessel, comprising:
   a. an occlusion catheter for insertion into the blood vessel at an incision downstream of the damaged section;
   b. an expandable and collapsible, nonporous stopper at the proximal end of the occlusion catheter which is expanded upstream of the damaged section to block the flow of blood through the vessel;
   c. a generally tubular prosthetic graft of a length longer than the damaged section of the vessel;
   d. a second catheter, covered by the graft and having a portion expandable in diameter, for insertion of the graft into the vessel;
   e. an adhesive applied to the outer periphery of the graft; and
   f. means for expanding the portion of the second catheter to effect contact and adhesion of the outer periphery of the graft to healthy portions of the vessel.

9. The apparatus for repairing within the body a damaged section of a blood vessel as defined in claim 8, wherein said stopper includes:
   a. a forward ring member;
   b. a rearward ring member fixed to the proximal end of the occlusion catheter;
   c. a plurality of radially extended rib members hingedly attached at their inner ends to the forward ring member;
   d. a plurality of support members each hingedly attached at its inner end to the rearward ring member and at its forward end to one of the plurality of rib members;
   e. a nonporous cover over the forward ring member and the plurality of rib members;

f. a helical spring located between the forward and rearward ring members; and g. a control cord attached to the center of the cover and extended along the central axis of the occlusion catheter and outwardly from the distal end of the occlusion catheter, which cord is pulled to compress the spring and expand the transverse diameter of the stopper, and which cord is released to permit the spring to extend to collapse the stopper.

10. The apparatus for repairing within the body a damaged section of a blood vessel as defined in claim 9, wherein:

a. the control cord is hollow and communicates from the distal end of the occlusion catheter to a plurality of dye ports for the emission of dye upstream and downstream of the cover.

11. Apparatus for repairing within the body an infrarenal abdominal aortic aneurysm, comprising:

a. an occlusion catheter for insertion into an incision in the femoral artery;

b. an expandable and collapsable, nonporous stopper at the proximal end of the occlusion catheter, which stopper is expanded within the aorta upstream of the aneurysm but downstream of the renal arteries to block the flow of blood through the aneurysm and the femoral arteries but not through the renal arteries;

c. a generally tubular prosthetic graft of double-woven Dacron having a length greater than that of the aneurysm;

d. an adhesive applied to the outer periphery of the graft;

e. a collapsed balloon catheter which temporarily receives as a sleeve the graft and which is inserted into the femoral artery and aorta about the occlusion catheter;

f. a protective sleeve which temporarily covers the graft during insertion into the aorta; and g. compressed gas to inflate the balloon catheter to contact and adhere to healthy sections of the aorta on either side of the aneurysm sections of the graft exposed by withdrawal of the protective sleeve.

* * * * *